US006559283B2

(12) United States Patent
Drauz et al.

(10) Patent No.: US 6,559,283 B2
(45) Date of Patent: May 6, 2003

(54) POLY-β-AMINO ACIDS, PREPARATION AND USE

(75) Inventors: Karlheinz Drauz, Freigericht (DE); Olaf Burkhardt, Kalmthout (BE); Stan M. Roberts, Parlegate Neston (GB); John Skidmore, Liverpool (GB); Paul Coffey, St. Helens (GB)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/880,122

(22) Filed: Jun. 14, 2001

(65) Prior Publication Data

US 2002/0038042 A1 Mar. 28, 2002

(30) Foreign Application Priority Data

Jun. 15, 2000 (DE) ......................... 100 29 596

(51) Int. Cl.[7] ..................... A61K 38/00; C07K 16/00; C07K 17/00; C07K 5/00; C07D 301/03
(52) U.S. Cl. ................ 530/332; 549/523; 549/524; 549/531
(58) Field of Search ................ 530/332; 549/513, 549/518, 523, 524, 531

(56) References Cited

U.S. PATENT DOCUMENTS

| 4,734,286 | A | * | 3/1988 | Mahieu et al. | ............... 424/489 |
| 6,060,585 | A | * | 5/2000 | Gellman et al. | ............ 530/323 |
| 6,225,482 | B1 | * | 5/2001 | Drauz et al. | ................. 549/525 |

FOREIGN PATENT DOCUMENTS

| DE | 100 03 110 | 9/2000 |
| EP | 1 006 111 | 6/2000 |
| EP | 1 006 127 | 6/2000 |

OTHER PUBLICATIONS

"Probing the Helical Secondary Structure of Short–Chain–b–Peptides" Seebach et al. Helvetical Chimica Acta. vol. 79 pp. 2043–2066. (1996).*
"How to Stabilize or Break b–Peptidic Helices by Disulfide Bridges: Synthesis and CD Investigation of b–Peptides with Cysteine and Homocysteine Side Chains" Jacobi et al. Helvetica Chimica Acta. vol. 82 pp. 1150–1172 (1999).*
Cappi et al, "New procedures for the Julia–Colonna asymmetric epoxidation: synthesis of (+)–clausenamide" Chem. Commun., p. 1159–1160 (1998).*
Ebrahim and Wills, "Synthetic applications of polymeric alpha–amino acids" Tetrahedron: Asymmetry, vol. 8(19), pp. 3163–3173 (1997).*
Navas et al, "Analysis of the Helical Conformations in Poly(beta–1–aspartate)s: Poly(alpha–n–butyl–beta–1–aspartate) and Poly(alpha–(2–methoxyethyl)–beta–1–aspartate)" Macromolecules, vol. 28, pp. 4487–4494 (1995).*
Munoz–Guerra et al, "Electron Microscopy Study of Crystalline Polymorphism of Helical Polyamide Poly(alpha–i–sobutyl–1–aspartate)" Macromolecules, vol. 22, pp. 1540–1545 (1989).*
Dini et al, "A Study of Platinum–Polyamide Catalysts. Catalytic Behaviour in the Benzene Hydrogenation Reaction" J. Catalysis vol. 30, pp. 1–12 (1973).*
David S. Breslow, et al., "Synthesis of Poly–β–Alanine from Acrylamide. A Novel Synthesis of β–Alanine," *The Journal of American Chemical Society*, vol. 79, 1957, pp. 3760–3763.
Dieter Seebach, et al., "β–Peptides: Synthesis by *Arndt–Eistert* Homologation with Concomitant Peptide Coupling Structure Determination by NMR and CD Spectroscopy and by X–Ray Crystallography," *Helvetica Chimica Acta*, vol. 79, (1996), pp. 913–941.
Sebastian Rissom et al., "Asymmetric Reduction of Acetophenone in Membrane Reactors: Comparison of Oxazaborolidine and Alcohol Dehydrogenase Catalysed Processes," *Tetrahedron: Asymmetry*, vol. 10, pp. 923–928, 1999.
J. Kovacs, et al., "Poly–β–L–Aspartic Acid. Synthesis Through Pentachlorophenyl Active Ester and Conformational Studies," *J. Am. Chem. Soc.*, vol. 87, (1965), pp. 119–120.
Gilles Guichard et al., "Solid–Phase Synthesis of β–Oligopeptides," *Chimia*, vol. 51, pp. 315–318, 1997.
Roger E. Marti et al., "Solid Phase of Synthesis of β–Peptides via Arndt–Eistert Homologation of Fmoc–Protected Amino Acid Diazoketones," *Tetrahedron Letters*, vol. 38, pp. 6145–6148, 1997.
Montserrat Garcia–Alvarez et al., "Conformation and Crystal Structure of Poly(α–cycloalkyl–β–L–aspartate)s," *J. Phys. Chem.*, vol. 101, pp. 4215–4223, 1997.

* cited by examiner

*Primary Examiner*—Richard L. Raymond
*Assistant Examiner*—Zachary C. Tucker
(74) *Attorney, Agent, or Firm*—Oblon, Spivak, McClelland, Maier & Neustadt, P.C.

(57) ABSTRACT

Poly-β-amino acids and their use in catalytic organic reactions, especially in epoxidation procedures, are provided.

15 Claims, No Drawings

POLY-β-AMINO ACIDS, PREPARATION AND USE

BACKGROUND OF THE INVENTION

1. Field of the Invention

The present invention relates to the use of homochiral poly-β-amino acids as catalysts for enantioselective organic reactions, in particular for catalytic enantioselective epoxidation of carbon—carbon double bonds. Furthermore, special homochiral poly-β-amino acids and their preparation are provided.

2. Description of the Background

Catalytic enantioselective organic reactions are among the most well-known and important organic transformations for the introduction of enantioselectivity into organic molecules by synthetic means. Furthermore, in industry processes are preferred in which the catalyst can be recovered and reused. The combination of both aspects leads to most superior enantioselective processes suitable for large scale production of organic molecules.

Poly-β-peptides, known to textile chemists as Nylon-3 polymers, have been prepared and studied for the last 50 years. Two distinct approaches to the preparation of poly-β-peptides exist. Firstly, a number of polymerization reactions where a suitably activated monomer is polymerized, under more-or-less controlled conditions, to generate a range of polymer lengths, have been reported. This first approach has been developed largely with the textile industry in mind and thus the focus has been on the preparation of long polymer chains. In addition the polymerization method has found some application in the preparation of polymer chains for use in structural studies, i.e. for the preparation of β-analogues of poly-α-amino acids.

The second approach is to utilize stepwise peptide bond synthesis, in which a protected β-amino acid is coupled to the peptide chain, the protecting group removed and the sequence repeated. Clearly, this latter method has the advantage that defined primary structures can be prepared. Thus a range of monomers can be utilized and it is possible to prepare a range of defined length homopolymers. Within the field of stepwise synthesis two main approaches exist; solution phase and solid phase synthesis (D. S. Breslow, G. E. Hulse, and A. S. Matlack, J. Am. Chem. Soc., 1957, 79, 3760; J. Kovacs, R. Ballina, R. L. Rodia, D. Balasubramamnian, and J. Applequist, J. Am. Chem. Soc., 1965, 87, 119; H. R. Kricheldorf, α-Aminoacid-N-Carboxy Anhydrides and Related Heterocycles, ed., Springer-Verlag, 1987; H. R. Kricheldorf, 36. Anionic Ring-opening polymerization: NCAs, ed. G. Allen and J. C. Bevington; J. Sebenda, 35. Anion Ring-Opening Polymerization: Lactams, ed. G. Allen and J. C. Bevington; M. Garcia-Alveraz, A. Martínez de Ilarduya, S. León, C. Alemán, and S. Muñoz-Guerra, J. Phys. Chem. A, 1997, 101, 4215; G. Guichard and D. Seebach, Chimia, 1997, 51, 315; Seebach et al. Helv. Chim. Acta, 1996, 79, 913 u. 2043; Marti et al. Tetrahedron Lett. 1997, 38, 6145).

It is known that poly-α-amino acids are useful as catalysts in enantioselective organic reactions. In particular the epoxidation of carbon—carbon double bonds (EP 991233642.3 and EP 99123643.1) is described. Heretofore, nothing has been described about poly-β-amino acids with regard to their use as catalysts in enantioselective organic reactions.

SUMMARY OF THE INVENTION

It is an object of the present invention is to provide more catalysts suitable for enantioselective organic reactions.

It is another object to provide a method of catalyzing an enantioselective reaction.

Unexpectedly, homochiral poly-β-amino acids, in particular homochiral homo-poly-β-amino acids, can be used as catalysts in enantioselective organic reactions. In a preferred embodiment, homochiral poly-β-amino acids are used in the epoxidation of carbon—carbon double bonds (i.e. —C=C—). It is especially preferred to use supported or crosslinked poly-β-amino acids.

Accordingly, the objects of the present invention are accomplished with a method of catalyzing an enantioselective reaction, comprising:

reacting a substrate in the presence of a homochiral poly-β-amino acid under conditions to produce a product, wherein the product is enantiomeric and one enantiomer of the product is produced in excess.

The objects of the present invention are also accomplished with a supported or crosslinked homochiral poly-β-amino acid.

A more complete appreciation of the invention and many of the attendant advantages thereof will be readily obtained as the same becomes better understood by reference to the following detailed description.

DETAILED DESCRIPTION OF THE INVENTION

The reaction conditions used for epoxidation may be the same as those mentioned for poly-α-amino acids. Therefore, it is most favorable to conduct the epoxidation in a biphasic or triphasic system as described in EP 99123642.3 and EP 99123643.1, both incorporated herein by reference.

The epoxidation is preferably accomplished with $H_2O_2$ in any kind of modification, that means as aqueous solution, as a complex with nitrogen containing compounds, e.g. urea-hydrogen peroxide, as percarbonate, perborate, and any similar source of active oxygen. The substrates for the epoxidation are carbon—carbon double bonds in any kind of organic molecule. The described method runs especially well for carbon—carbon double bonds attached to an electron-withdrawing group, resulting in an electron-poor double bond. Substrates to be epoxidized are preferably those described in EP 99123642.3, incorporated herein by reference.

It is especially advantageous to use catalysts pertinent to the invention for enantioselective organic reactions because the insoluble catalysts can be recovered easily after usage and can be used again. Normally, the reaction mixtures are worked up using techniques well-known to those skilled in the art. The soluble products, i.e. the epoxides, are separated in an advantageous manner by filtering off the poly-β-amino acid and is worked up in an aqueous medium. If required, chromatography on silica gel or recrystallisation may then be performed for purification purposes. The insoluble catalysts can then be dried and reused.

The application of these new catalysts can be carried out in various ways. In many cases a simple batch process is preferable. A number of approaches to varying the properties of the catalysts have been taken; it is possible to use a range of supports and adsorbents which facilitate other methods of application. Here it is pertinent to mention the use as insoluble catalyst, which is—as discussed above—easy to separate by filtration and recycle as well as the use in a fixed-bed-column or a membrane reactor in a continuous process (DE 199 10 691.6; Rissom et al., Tetrahedron Asymmetry 1999, 10, 923–928, both incorporated herein by reference).

As can be seen in the working examples enantioselective induction on epoxidation by catalysts according to the invention is achieved in almost >70% ee at a conversion of >90%. The enantiomeric excess (ee) achieved in the present invention may be at least 5%, 10%, 15%, 25%, 50%, 75%, 80%, 85%, 90%, 95%, 98%, 99%, or 99.5% ee. The conversion may be at least 5%, 10%, 15%, 25%, 50%, 75%, 80%, 85%, 90%, 95%, 98%, 99%, or 99.5%.

In a additional embodiment, the present invention is directed to supported or crosslinked homochiral poly-β-amino acids, in particular homochiral homo-poly-β-amino acids.

The support can be fixed to the poly-β-amino acids by a covalent bond or by adsorption. Supports suitable for adsorptive means are well-known to those skilled in the art. In particular those selected from the group comprising $SiO_2$-containing compounds, nitrocellulose, cellulose or carbon black are preferred. Most preferred are those $SiO_2$-containing compounds described in EP 99123643.1, incorporated herein by reference. The amounts of poly-β-amino acids per unit support can also be deduced from EP 99123643.1, incorporated herein by reference.

Supports with regard to covalent bonding are preferably selected from the group comprising resins (i.e. epoxide-containing such as eupergit, Merrifield, Wang, Tentagel etc.) and polysiloxanes. Depending on the method of polymerisation [see: Kricheldorf, α-Aminoacid-N-Carboxy Anhydrides and Related Heterocycles, ed., Springer-Verlag, 1987, S.11, incorporated herein by reference], the support can be chosen any suitable polymer with an end-group which may be coupled to the amino acid chain. For that reason various polymers, which can be easily modified, can be used, i.e., polyethers (i.e. polyethylenglycols, polypropylenglycols), polystyrenes, polyacrylates, and a mixture of theses polymers.

Alternatively, poly-β-amino acids according to the invention may be crosslinked. This can be achieved by polyfunctionalised amines, i.e. those pertinent to EP 99123642.3, incorporated herein by reference. Preferred is the use of dendrimers, for example.

A further aspect the present invention relates to a process for the production of supported or crosslinked poly-β-amino acids. The polyamino acids according to the invention may be synthesised according to the techniques well-known to those skilled in the art.

Three main approaches to the preparation of the catalysts may be used. Firstly methods of stepwise synthesis may be employed. In this approach the coupling methods known to poly-alpha-amino acid chemists are applied to the present invention. This can be carried out either on solid phase or in solution. Secondly, a polymerization of a β-amino acid derivative with an activated carbonyl group (including but not limited to acid chlorides, anhydrides, esters etc) may be performed. Finally polymerization of the β-lactam corresponding to the amino acid may be performed in the presence of catalytic base (and on occasion a cocatalyst of acylated lactam). This latter method is preferred for the preparation of pure samples of long chain poly-β-amino acids.

The term homochiral poly-β-amino acid is to be understood in such a way that all β-amino acids of the chain are the same and possess the same chirality (homochiral homo-poly-β-amino acids) or at least domains responsible for the impact of chiral information on epoxidation have to be builtd of the same β-amino acids and possess the same chiral conformation. Hence, poly-β-amino acids may be derived from heterochiral α- or β-amino acids as long as the above mentioned domains are present within the molecule in question.

According to the invention B-amino acids can be substituted in 2- or 3-position or both, i.e such as described in following formula:

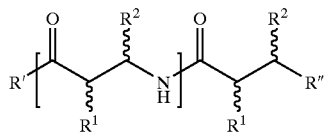

where
R$^1$, R$^2$ independently: H, residue of an amino acid, like alkyl, aryl, aralkyl, heteroaryl, provided not both R$^1$, R$^2$ are H, and
R', R" independently: polymer, OH, crosslinker, NHR$^1$, NH$_2$.

The alkyl, aryl, aralkyl, and heteroaryl groups may have from 1 to 20 carbon atoms, for example.

EXAMPLES

Having generally described this invention, a further understanding can be obtained by reference to certain specific examples which are provided herein for purposes of illustration only and are not intended to be limiting unless otherwise specified.

Preparation of β$^3$-L-Leucine

To N-β-Fmoc-L-leucine (4 g, 11.3 mmol), in dry diethyl ether: tetrahydrofuran (1:1), was added methyl chloroformate (0.87 ml, 1 equiv.), and triethylamine (1.58 ml, 1 equiv.), and the reaction was stirred at −10° C. for two hours. After this the precipitated triethylamine hydrochloride was separated by filtration and to the remaining solution was added freshly prepared ethereal diazomethane with vigorous stirring, until a bright yellow colour persisted. This was stirred at room temperature overnight and any remaining excess of diazomethane was removed by bubbling a gentle stream of nitrogen through the solution. This was then concentrated under reduced pressure to give a viscose yellow oil, which was dissolved in dioxane (50 ml), and added dropwise to an aqueous solution of sodium carbonate (1 equiv.), sodium thiosulphate (1 equiv.), and a catalytic amount of silver trifluoroacetate, which was kept at between 80–85° C. for eight hours. The dioxane was then removed under reduced pressure, the product was extracted into ethyl acetate, separated, dried over magnesium sulphate and concentrated in vacuo. It was purified by chromatography on silica, (5% loading), with hexane:ethyl acetate, 3:2 as eluent followed by recrystallisation from hexane/ethyl acetate to give the product as a white crystalline solid in 25% overall yield.

Solid Phase Peptide Synthesis

Solid phase synthesis of an oligopeptide was carried out using an automated peptide synthesiser. The synthesis employed Fmoc protection chemistry and the activated carboxyl of each subsequent amino acid was attached to the deprotected amino group of the previous, starting with the desired first residue already being attached to the Wang resin. The Fmoc deprotection was achieved with a 20% piperidine/DMF solution, activation was with a 5% NNM/DMF solution, and a fourfold excess of each amino acid, and PyBOP was used for each coupling step. The peptide can be cleaved from the resin with a mixture of TFA/TES/H$_2$O/DCM.

β-Methyl-(2R)-N-(9-fluorenylmethoxycarbonyl)amino Acid-Wang Resin

To a suspension of Wang resin of known weight and loading (usually between 0.5 and 1 g and 0.2 to 1 mmol OH/g), in dry DMF (5 cm$^3$) was added the desired Fmoc protected amino acid (4 equiv.), and the mixture was stirred at room temperature, under nitrogen for 15 minutes. Pyridine (4 equiv.) and 2,6-dichlorobenzoyl chloride (4 equiv.) were added and the suspension stirred at room temperature for 24 h.

This was then filtered, and washed with DMF (25 cm$^3$), DCM (25 cm$^3$) and methanol (25 cm$^3$), and the % loading was checked, according to the method outlined below, and found to be between 70 and 90%. The remaining OH groups of the resin were benzoylated with benzoyl chloride in pyridine for 2 h. This was then filtered, washed with the same combination of, and quantities of solvents as before, and the loaded resin was dried and rechecked for percentage loading.

Method of Estimation of First Residue Attachment (Novabiochem)

Dry Fmoc-amino acid-resin (2 mg) was placed into two 10 mm matched silica UV cells and to these was added 20% piperidine in DMF (3 cm$^3$). Each of these cells were agitated in turn for 5 minutes before being placed in the spectrometer, and having their absorbance at 290 nm measured against a 3rd matched reference cell containing 20% piperidine in DMF (3 cm$^3$). The average of the two values obtained was used to calculate the percentage loading from the graph printed in the Novabiochem catalogue.

The degree of successful coupling of subsequent attachment can be monitored in a similar manner during the deprotection steps.

The procedure for the β-leucine epoxidations were as follows:

Biphasic system—the catalyst 20-β-L-Leu-Resin (100 mg 0.18 mmol/g) was stirred in dry toluene in the presence of DBU (56 μl) for 16 h. The following day trans-chalcone (50 mg) and UHP (28 mg) were added in dry THF (1 ml).

| Time (hours) | 0.5 | 1* | 2 | 4* | 8 | 24 |
|---|---|---|---|---|---|---|
| ee % | 76 | 67 | 53 | 45 | 41 | 39 |
| conv % | 24 | 31 | 59 | 72 | 88 | 96 |

*further addition of DBU (56 μlmicrol) and UHP (28 mg) after sampling.

Triphasic system—the catalyst 19-β-L-Leu-aalpha-L-Leu-Resin (100 mg, 0.18 mmol/g) was stirred in toluene (0.5 ml) in the presence of aqueous NaOH (4M 0.5 ml) for over the weekend (60 h). To this was added trans-chalcone (50 mg) and 30% aqueous hydrogen peroxide solution (0.7 ml) and toluene (0.5 ml)

| Time (hours) | 0.5 | 1 | 2 | 4 | 8 | 24 | 30 |
|---|---|---|---|---|---|---|---|
| ee % | 16 | 30 | 28 | 45 | 68 | 70 | 72 |
| conv % | 1 | 3 | 6 | 16 | 59 | 92 | 92 |

Obviously, numerous modifications and variations of the present invention are possible in light of the above teachings. It is therefore to be understood that within the scope of the appended claims, the invention may be practiced otherwise than as specifically described herein.

This application is based on German Patent Application Serial No. 100 29 596.7, filed on Jun. 15, 2000, and incorporated herein by reference.

What is claimed is:

1. A supported or crosslinked homochiral homo-poly-β-amino acid catalyst attached by a covalent bond to a solid support selected from the group consisting of polysiloxanes, polyethers, polystyrenes, and polyacrylates or attached by adsorption to a solid support selected from the group consisting of SiO$_2$-containing compounds, nitrocellulose, and cellulose.

2. The homochiral homo-poly-β-amino acid of claim 1, which is crosslinked.

3. The homochiral homo-poly-β-amino acid of claim 1, wherein the poly-β-amino acid is fixed to the support by a covalent bond to a solid support selected from the group consisting of polysiloxanes, polyethers, polystyrenes, and polyacrylates.

4. The poly-β-amino acid of claim 1, wherein the poly-β-amino acids is fixed to the support by adsorption.

5. The poly-β-amino acid according to claim 1, wherein crosslinking is achieved by polyfunctionalized amines.

6. A process for the production of the poly-β-amino acid of claim 1, comprising synthesizing the poly-β-amino acid by solid-phase methodology.

7. A method of catalyzing an enantioselective reaction, comprising:

reacting a substrate in the presence of the supported or crosslinked homochiral homo-poly-β-amino acid of claim 1 under conditions to produce a product, wherein the product is enantiomeric and one enantiomer of the product is produced in excess.

8. The method of claim 7, wherein the substrate is an olefin, the product is an epoxide, and the reaction is conducted in the presence of an epoxidizing agent.

9. The method of claim 8, wherein the epoxidizing agent is hydrogen peroxide.

10. The method of claim 8, wherein the reaction is conducted in a biphasic or triphasic reaction mixture.

11. The method of claim 7, wherein the homochiral homo-poly-β-amino acid is crosslinked.

12. The method of claim 7, wherein the homochiral homo-poly-β-amino acid is attached to the solid support selected from the group consisting of polysiloxanes, polyethers, polystyrenes, and polyacrylates.

13. The method of claim 12, wherein the homochiral homo-poly-β-amino acid is attached by adsorption to a solid support selected from the group consisting of SiO$_2$-containing compounds, nitrocellulose, and cellulose.

14. The method of claim 7, wherein the product has an enantiomeric excess of at least 50% ee.

15. The homochiral homo-poly-β-amino acid of claim 1, which is attached by adsorption to a solid support selected from the group consisting of SiO$_2$-containing compounds, nitrocellulose, and cellulose.

* * * * *